United States Patent [19]

Ogata et al.

[11] Patent Number: 5,229,378
[45] Date of Patent: Jul. 20, 1993

[54] GLYCYRRHETIC ACID DERIVATIVES

[75] Inventors: Kazumi Ogata, Toyonaka; Kyouzo Yamamoto, Higashiosaka; Reiko Matsuda, Osaka, all of Japan

[73] Assignee: Senju Pharmaceutical Co., Ltd., Osaka, Japan

[21] Appl. No.: 849,574

[22] Filed: Mar. 10, 1992

[30] Foreign Application Priority Data

Mar. 13, 1991 [JP] Japan .................................. 3-128799

[51] Int. Cl.$^5$ ...................... A61K 31/665; C07F 9/28
[52] U.S. Cl. .................................. 514/99; 549/222; 560/6
[58] Field of Search ............... 514/99; 560/6; 549/222

[56] References Cited

U.S. PATENT DOCUMENTS

| | | | |
|---|---|---|---|
| 3,452,078 | 6/1969 | Turner et al. | 560/6 |
| 3,734,944 | 5/1973 | Turner | 560/6 |
| 3,742,021 | 6/1973 | Turner | 560/6 |
| 4,061,773 | 12/1977 | Chan | 560/6 |
| 4,939,128 | 7/1990 | Kato et al. | 540/5 |

FOREIGN PATENT DOCUMENTS

| | | | |
|---|---|---|---|
| 339486 | 1/1989 | European Pat. Off. | 549/222 |
| 1805958 | 5/1969 | Fed. Rep. of Germany | 549/222 |
| 2001906 | 10/1970 | Fed. Rep. of Germany | 560/6 |
| 15968 | 6/1970 | Japan | 540/5 |
| 1093908 | 12/1967 | United Kingdom | 560/6 |

OTHER PUBLICATIONS

Riess et al, Bull. Soc. Chim France No. 6, 1961 pp. 1243-1244.

*Primary Examiner*—Cecilia Tsang
*Attorney, Agent, or Firm*—Wenderoth, Lind & Ponack

[57] ABSTRACT

Presented are a glycyrrhetic acid derivative of the following formula or a pharmacologically acceptable salt thereof, which has antioxidant, antiinflammatory and/or antiallergic activity, a process for producing said compound or salt, and an antioxidant, antiinflammatory and/or antiallergic composition comprising said compound or salt.

21 Claims, 3 Drawing Sheets

GLYCYRRHETIC ACID DERIVATIVES

FIELD OF THE INVENTION

The present invention relates to novel and useful glycyrrhetic acid derivatives, a process for producing the same, and uses for said derivatives. More particularly, the present invention relates to 3-(L-ascorbyl-2-phosphoryl)-glycyrrhetic acid, an ester derivative thereof, or a pharmacologically acceptable salt thereof, a process for producing the same, and an antioxidant, antiinflammatory and/or antiallergic composition comprising the same.

BACKGROUND OF THE INVENTION

Heretofore, ascorbic acid has been used as an antiscurvy drug. It is also known that ascorbic acid is involved in collagenation and inhibits production of melanins in the body. Recently, it has been reported that this substance has anticancer activity as well. On the other hand, glycyrrhetic acid is known to have antiinflammatory activity. However, neither of these compounds is satisfactory enough in efficacies.

Therefore, the inventors of the present invention searched for new more active compounds and found, as a consequence, that a novel compound corresponding to ascorbic acid and glycyrrhetic acid linked together through a phosphoric acid residue meets the above object. The present invention has been conceived and developed on the basis of the above finding.

SUMMARY OF THE INVENTION

The present invention, therefore, provides a compound of the following formula

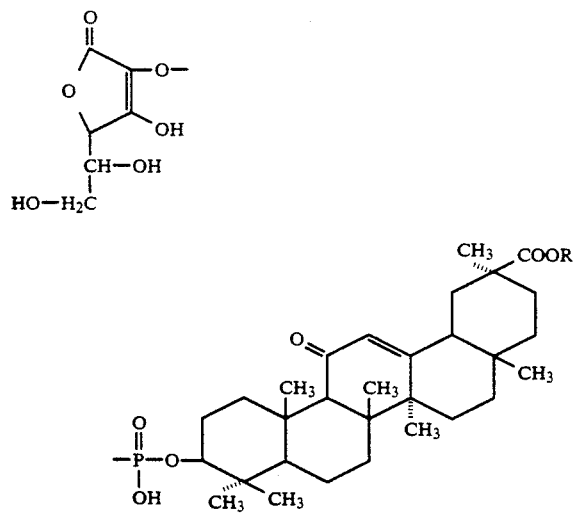

or a pharmacologically acceptable salt thereof, a process for producing said compound or salt, and an antioxidant, antiinflammatory and/or antiallergic composition comprising said compound or salt.

Referring to the above formula, R means a hydrogen atom or an alkyl group which contains preferably 1 to 18 carbon atoms. The carbon chain of the alkyl group may be linear, branched or cyclic and may even have a ring structure. Furthermore, such alkyl group may optionally be substituted by other groups. As such, the alkyl group includes lower alkyl groups such as methyl, ethyl, n-propyl, i-propyl, cyclopropyl, n-butyl, t-butyl, sec-butyl, n-pentyl, 1-ethylpropyl, i-pentyl, n-hexyl, etc., higher alkyl groups such as n-decyl, n-heptadecyl, n-octadecyl, etc., inclusive of isomers thereof, and benzyl.

The pharmacologically acceptable salt of the invention includes, among others, alkali metal salts such as sodium salt, potassium salt, etc. and alkaline earth metal salts such as calcium salt, magnesium salt and so on. However, any other salts, insofar as they are pharmacologically acceptable, can be synthesized and used with advantage.

DETAILED DESCRIPTION OF THE INVENTION

The compound of the present invention can be synthesized, for example as follows. Thus, (1) glycyrrhetic acid or an alkyl ester thereof is reacted with a halophosphorylating agent, (2) the reaction product is then reacted with ascorbic acid with its 5and 6-hydroxy groups previously protected and (3) finally the protective groups are removed by hydrolysis.

In this process for production of the compound of the invention, glycyrrhetic acid or an alkyl ester thereof is reacted with a halophosphorylating agent in the first place. Generally, this reaction is preferably conducted in the presence of an acid acceptor.

The halophosphorylating agent can be any compound with which a halophosphoric acid residue can be introduced into the hydroxyl group of glycyrrhetic acid or an alkyl ester thereof and is preferably phosphoryl chloride or phosphoryl bromide, for instance. While the acid acceptor for use in this reaction may be any acid acceptor substance that is generally used in reactions of this type, it is preferably an organic amine such as pyridine or triethylamine.

The halophosphorylation reaction in the process of the invention generally proceeds smoothly in an appropriate solvent. The solvent may be any solvent that does not interfere with the reaction, and generally aromatic hydrocarbons such as benzene, toluene, etc. and halogenated hydrocarbons such as methylene chloride, chloroform, etc. can be advantageously employed.

While the conditions of this reaction should, of course, be selected so as to insure the smoothest possible progress of the reaction, generally this reaction is preferably conducted at a temperature of about 0° C. to about 50° C. In this temperature range, the reaction goes to completion in about 1 to 10 hours.

The glycyrrhetic acid or alkyl ester halophosphorylated in the above manner is then reacted with ascorbic acid whose hydroxy groups in the 5- and 6-positions have been previously protected. The protective groups in the 5- and 6-positions of this protected ascorbic acid may be any hydroxy-protecting groups that can be easily eliminated after the reaction. Thus, acyl groups such as acetyl may be employed for this purpose but an alkylidene group such as isopropylidene, benzylidene or the like is preferred.

The reaction of said halophosphorylated glycyrrhetic acid or alkyl ester thereof with said ascorbic acid previously protected in the 5- and 6-positions is preferably conducted in a nonpolar solvent. While ethers such as dioxane and tetrahydrofuran are preferred examples of the nonpolar solvent, other nonpolar solvents that do not adversely affect the reaction can also be selectively employed. This reaction generally proceeds smoothly in the presence of an acid acceptor.

The preferred acid acceptor is an organic amine such as pyridine and triethylamine. This reaction generally proceeds advantageously at a temperature of about 0° C. to 50° C. and goes to completion generally in about 1 to 10 hours.

Then, removal of the hydroxy-protecting groups from the 5- and 6-positions of the ascorbic acid moiety and the halogen atom from the halophosphoric acid residue moiety gives the object compound of the invention. This removal of the protective groups is preferably effected by hydrolysis. This hydrolysis reaction is preferably conducted in the presence of an acid. As the acid just mentioned, inorganic acids such as hydrochloric acid, sulfuric acid, phosphoric acid, etc. and organic acids such as acetic acid, citric acid, etc. can be advantageously employed. The hydrolysis reaction is preferably conducted in an appropriate hydrous solvent. Thus, a mixture of water and a water-miscible organic solvent can be employed with advantage. The preferred water-miscible solvents are methanol, ethanol, dioxane, tetrahydrofuran and so on.

The conditions of hydrolysis reaction are selected so that all the protective groups can be successfully eliminated. Generally, this hydrolysis reaction proceeds smoothly at a temperature of about 0° C. to about 60° C. and, in many instances, goes to completion in about 1 to 2 hours.

The compound of the invention thus produced can be converted to a pharmacologically acceptable salt and isolated as such, using pertinent procedures which are known per se. Thus, the compound obtained as above can be easily converted to such a salt by, for example, reacting it with an alkali metal or alkaline earth metal ion donor compound in an appropriate solvent. Conversion to the salt may be carried out after isolation of the compound of the invention from the reaction mixture or without prior isolation. The metal ion donor compound may for example be the corresponding hydroxide, carbonate or hydrogen carbonate and any of them can be used with advantage.

The compound of the invention which can be obtained in the above manner is a novel compound which has not been described in the literature and has antioxidant, antiinflammatory and antiallergic activities as well as an action to stabilize compounds which are ready to absorb ultraviolet light or liable to be decomposed and even a cosmetic action. Therefore, the compound is very useful for such purposes.

Having the above-mentioned multiple actions, the compound of the invention is not only of value as a medicine, such as an antioxidant an antiinflammatory agent or an antiallergic agent, but also as a cosmetic ingredient.

The typical diseases which can be treated with the antioxidant agent according to the invention are cataract and various ischemic organic diseases.

As an antiinflammatory agent, the compound of the invention may be indicated in a variety of inflammatory diseases such as hemorrhoids, rheumatoid arthritis, rheumatism deformans, spondylosis deformans, arthrosis deformans, lumbago, gout attack, acute otitis media, cystitis, prostitis, toothache, uveitis, sinusitis and so on. In these diseases, the compound can be used advantageously for therapeutic purposes.

For use as an antiallergic agent, the compound of the invention can be indicated in various allergic diseases such as bronchial asthma, pollinosis, allergic rhinitis, dietary allergic gastritis, allergic diarrhea, ulcerative colitis, stomatitis, nodular periarteritis, obliterating endarteritis, endocarditis, urticaria, eczema, contact dermatitis, phlyctenosis, sympathetic ophthalmitis, allergic conjunctivitis, allergic keratitis and so on. In any of these diseases, the compound can be used advantageously for therapeutic purposes.

For use as a cosmetic ingredient, the compound of the invention can be incorporated in such formulations as creams, lotions, toilet water, etc. for absorption of ultraviolet light, for skin conditioning or for purposes of stabilizing other cosmetic ingredients.

The antioxidant, antiinflammatory and/or antiallergic composition of the invention may contain one species or more than one species, in a suitable combination, of the compound of the invention according to the intended application.

The antioxidant, antiinflammatory and/or antiallergic composition of the invention can be administered orally or otherwise for the prevention or treatment of the above-mentioned diseases. With regard to the dosage forms that can be employed, various solid preparations such as tablets, granules, powders, capsules, ointments, suppositories, etc. and liquid preparations such as eyedrops, injections, syrups, etc. can be manufactured by procedures known per se. In the manufacture of such preparations, various excipients which are commonly employed for pharmaceutical purposes, such as binders, disintegrators, thickeners, dispersants, reabsorption promoters, corrigents, buffers, surfactants, solubilizers, preservatives, emulsifiers, isotonizing agents, stabilizers, pH adjusting agents, etc., can be incorporated as necessary. In formulating the compound of the invention into cosmetic products, too, the ingredients generally employed in the cosmetic industry can be selectively employed in conjunction.

The medical dosage of the compound of the invention depends on the particular species of compound, the patient's age and body weight, the dosage form used, the type and condition of disease and other conditions. In the case of an injectable preparation, for instance, the daily dosage for an adult patient may range from about 1 mg to about 100 mg. As to an oral preparation, about 10 mg to 1000 mg per dose can be administered a few times a day. For use as an eye drop, a solution of about 0.1 to 5 w/v % concentration can be instilled, a few drops a time, several times a day.

The concentration of the compound of the invention in a cosmetic product should vary with the particular species of compound, the type of cosmetic product, the purpose for which the compound is added and other conditions. Generally, however, it is used in the concentration range of about 0.001 to 5 w/w % and preferably in the range of about 0.01 to 2 w/w %.

Unless contrary to the object of the invention, the composition of the invention may contain appropriate amounts of other antioxidants, antiinflammatory and/or antiallergic agents and/or other medicinally active ingredients.

EXAMPLES

The following examples and test examples are intended to describe the invention in further detail and should by no means be construed as defining the scope of the invention.

EXAMPLE 1

3-(L-ascorbyl-2-phosphoryl)-glycyrrhetic acid

To a mixture of 4.7 g of glycyrrhetic acid and 8 ml of dry pyridine is added 30 ml of dry chloroform and while the solution is stirred with ice-cooling, a solution of 3.2 of phosphoryl chloride in 30 ml of dry benzene is added dropwise. The mixture is stirred under ice-cooling for 30 minutes and then at room temperature for 1.5 hours. This reaction mixture is concentrated under reduced pressure and the residue is dissolved in 20 ml of benzene. This benzene solution is added dropwise to a mixture of 4 g of isopropylideneascorbic acid and 2.5 ml of dry pyridine in 30 ml of dry tetrahydrofuran and the mixture is stirred with ice-cooling for 30 minutes and further at room temperature for 2 hours. The reaction mixture is then concentrated under reduced pressure. To the residual oil are added 50 ml of ethanol and 20 ml of 0.5N-hydrochloric acid and the mixture is stirred at 60° C. for 30 minutes for deacetonization. After cooling, the reaction mixture is extracted with ethyl acetate and the extract is washed with saturated aqueous sodium chloride solution and dried over anhydrous sodium sulfate. The solvent is then distilled off under reduced pressure. To the residue is added n-hexane, the mixture is allowed to stand and the resulting crystals are collected by filtration. Recrystallization from n-hexane-acetone provides 2.9 g of white crystals. m.p. 150–153 (decomp.). Silica gel TLC (developing solvent=chloroform: methanol: water=65:25:4): Rf=0.30.

Elemental analysis, for $C_{36}H_{53}O_{12}P \cdot 2H_2O$. Calcd. C: 58.05 H: 7.71. Found C: 58.37 H: 7.85.

IR: $\nu_{KBr}$: 3432, 2976, 1734, 1608 cm$^{-1}$.

EXAMPLE 2

Methyl 3-(L-ascorbyl-2-phosphoryl)-glycyrrhetinate

In 30 ml of dry chloroform are dissolved 5 g of methyl glycyrrhetinate and 8 ml of dry pyridine and a solution of 3.2 g of phosphoryl chloride in 30 ml of dry benzene is added dropwise to the above solution under ice-cooling and stirring. The mixture is stirred with ice-cooling for 30 minutes and then at room temperature for 1.5 hours. The reaction mixture is then concentrated under reduced pressure and the residue is dissolved in 20 ml of benzene. This benzene solution is added dropwise to a mixture of 4 g of isopropylideneascorbic acid and 2.5 ml of dry pyridine in 30 ml of dry tetrahydrofuran and the mixture is stirred with cooling for 30 minutes and then at room temperature for 3 hours. The reaction mixture is then concentrated under reduced pressure. To the residual oil are added 50 ml of ethanol and 20 ml of 0.5-N-hydrochloric acid and the mixture is stirred at 60° C. for 30 minutes for deacetonization. After cooling, the reaction mixture is extracted with ethyl acetate and the extract is washed with saturated aqueous sodium chloride solution and dried over anhydrous sodium sulfate. The solvent is then distilled off under reduced pressure. To the residue is added n-hexane, the mixture is allowed to stand and the resulting crystals are collected by filtration and recrystallized from n-hexane-acetone to provide 2.5 g of white crystals. m.p. 135°–138° C. (decomp.). Silica gel TLC (developing solvent=chloroform:methanol:water=65:25:4): Rf=0.32.

Elemental analysis, for $C_{37}H_{55}O_{12}p \cdot 3H_2O$. Calcd. C: 57.21 H: 7.91. Found. C: 57.53 H: 7.85.

IR: $\nu_{KBr}$: 3424, 2932, 1730, 1662 cm$^{-1}$.

EXAMPLE 3

Ethyl 3-(L-ascorbyl-2-phosphoryl)-glycyrrhetinate

The reaction procedure of Example 2 is repeated using 4.8 g of ethyl glycyrrhetinate and the reaction product is recrystallized from n-hexane-acetone to give 2.8 g of white crystals. m.p. 130°–132° C. (decomp.). Silica gel TLC (developing solvent=chloroform:methanol:water=65:25:4): Rf=0.33.

Elemental analysis, for $C_{38}H_{57}O_{12}p \cdot 2H_2O$. Calcd. C: 59.06 H: 7.96. Found C: 59.34 H: 7.96.

IR: $\nu_{KBr}$: 3424, 2932, 1730, 1652 cm$^{-1}$.

EXAMPLE 4

Hexyl 3(L-ascorbyl-2-phosphoryl-glycyrrhetinate potassium

The reaction procedure of Example 2 is repeated using 5.5 g of hexyl glycyrrhetinate to give an oil. This oil is dissolved in 30 ml of ethanol and a solution of potassium hydroxide in ethanol is gradually added dropwise until the solution becomes pH 5–6, whereupon white crystals separate out. The crystals are collected by filtration and recrystallized from n-hexane-acetone to provide 2.5 g of white crystals. m.p. 215°–217° C. (decomp.). Silica gel TLC (developing solvent=chloroform:methanol:water=65:25:4): Rf=0.35.

Elemental analysis, for $C_{42}H_{63}O_{12}PK_2$. Calcd. C: 58.04 H: 7.31. Found C: 58.28 H: 7.61.

IR: $\nu_{KBr}$: 3432, 2976, 1734, 1608 cm$^{-1}$.

EXAMPLE 5

Lauryl 3-(L-ascorbyl-2-phosphoryl)-glycyrrhetinate potassium

The reaction procedure of Example 2 is repeated using 6.4 g of lauryl glycyrrhetinate to give an oil. This oil is dissolved in 30 ml of ethanol and a solution of potassium hydroxide in ethanol is gradually added dropwise until the solution becomes pH 5–6. The resulting white crystals are collected by filtration and recrystallized from chloroform-acetone to give 2.6 g of white crystals. m.p. 212°–215° C. (decomp.). Silica gel TLC (developing solvent=chloroform:methanol:water=65:25:4): Rf=0.42.

Elemental analysis, for $C_{48}H_{75}O_{12}PK_2$. Calcd. C: 60.47 H: 7.93. Found C: 60.54 H: 8.10.

IR: $\nu_{KBr}$: 3432, 2928, 1730, 1652 cm$^{-1}$.

EXAMPLE 6

Stearyl 3-(L-ascorbyl-2-phosphoryl)-glycyrrhetinate potassium

The reaction procedure of Example 2 is repeated using 7.4 g of stearyl glycyrrhetinate to give an oil. This oil is dissolved in 30 ml of ethanol and a solution of potassium hydroxide in ethanol is gradually added dropwise until the solution becomes pH 5–6. The resulting white crystals are collected by filtration and recrystallized from chloroform-acetone to give 2.2 g of white crystals. m.p. 208°–210° C. (decomp.). Silica gel TLC (developing solvent=chloroform:methanol:water=65:25:4): Rf=0.46.

Elemental analysis, for $C_{54}H_{87}O_{12}PK_2$. Calcd. C: 62.52 H: 8.45. Found C: 62.80 H: 8.38.

IR: $\nu_{KBr}$: 3432, 2976, 1734, 1608 cm$^{-1}$.

TEST EXAMPLE 1

Antioxidant activity assay

The antioxidant activity of the compound of the invention was assayed by the method of Stocks.

This experiment was performed using male Wistar rats (about 10 weeks old). After perfusion for removal of blood from the brain, the brain tissue was removed and homogenized in 4 volumes of ice-cooled 0.1M phosphate-NaCl buffer (pH 7.4). The homogenate was centrifuged at 1000×g for 10 minutes and the supernatant was taken. The brain homogenate was diluted with 10 volumes of phosphate-NaCl buffer and a 500 μl portion of the dilution was incubated at 37° C. for 60 minutes. The reaction was quenched by pouring the incubate in ice-water and 490 μl of 0.1M phosphate-NaCl buffer was added. The amount of lipid peroxide (LPO) was determined by the TBA method. The amount of LPO was expressed in the amount of malondialdehyde (MDA) per mg protein. The amount of protein was determined by the method of Lowry.

Test compounds (1) Methyl 3-(L-ascorbyl-2-phosphoryl)-glycyrrhetinate
(2) Ethyl 3-(L-ascorbyl-2-phosphoryl)-glycyrrhetinate
(3) Hexyl 3-(L-ascorbyl-2-phosphoryl)-glycyrrhetinate potassium The results are set forth in Table 1.

TABLE 1

| Compound | Dosage (M) | % Inhibition |
|---|---|---|
| (1) | $1 \times 10^{-3}$ | 95.3 |
|     | $1 \times 10^{-4}$ | 87.6 |
| (2) | $1 \times 10^{-3}$ | 95.4 |
|     | $1 \times 10^{-4}$ | 44.7 |
| (3) | $1 \times 10^{-3}$ | 94.8 |
|     | $1 \times 10^{-4}$ | 82.5 |

The above results indicate that the compound of the invention has satisfactory antioxidant activity.

TEST EXAMPLE 2

Antiinflammatory activity assay

The antiinflammatory activity of the compound of the invention was assayed by the mouse paw edema test. The experiment was performed in groups of 6 male ddy mice weighting 20 g-25 g. The volume of the right hind paw of each mouse was measured with a plethysmograph and 200 mg of the compound of the invention was orally administered. After 1 hour, 0.05 ml of 0.75% formalin as a phlogistic agent was injected subcutaneously into the dorsum of the right hind paw and the foot volume was measured at timed intervals. The edema rate and the percent inhibition was calculated from the values found.

$$\text{Edema rate (\%)} = \left( \frac{\text{Foot volume after injection of phlogistic agent}}{\text{Foot volume before injection of phlogistic agent}} - 1 \right) \times 100$$

Test compounds (1) Methyl 3-(L-ascorbyl-2-phosphoryl)-glycyrrhetinate
(2) Ethyl 3-(L-ascorbyl-2-phosphoryl)-glycyrrhetinate
(3) Hexyl 3-(L-ascorbyl-2-phosphoryl)-glycyrrhetinate potassium
(4) Lauryl 3-(L-ascorbyl-2-phosphoryl)-glycyrrhetinate potassium
(5) Stearyl 3-(L-ascorbyl-2-phosphoryl)-glycyrrhetinate potassium
(6) Glycyrrhetic acid The results are set forth in Table 2.

TABLE 2

| Compound | % Inhibition | |
|---|---|---|
|  | Hour 1 | Hour 4 |
| (1) | 36.36 | 37.84 |
| (2) | 18.84 | 28.72 |
| (3) | 22.50 | 22.07 |
| (4) | 49.03 | 50.57 |
| (5) | 31.02 | 34.42 |
| (6) | 16.28 | 25.37 |

The above results indicate that the compound of the invention has higher antiinflammatory activity than glycyrrhetic acid.

| Preparation Example 1 | Injection |
|---|---|
| 3-(L-Ascorbyl-2-phosphoryl)-glycyrrhetic acid | 100 mg |
| Glucose | 5 g |

The above ingredients are dissolved in distilled water for injection and the solution is adjusted to pH 6 with sodium hydroxide and made up to 100 ml. This solution is filtered and the filtrate is aseptically distributed, in 2 ml portions, into glass ampules, which are then sealed by fusion to provide an injectable solution.

| Preparation Example 2 | Ophthalmic solution |
|---|---|
| Ethyl 3-(L-ascorbyl-2-phosphoryl)-glycyrrhetinate | 0.3 g |
| Boric acid | 0.7 g |
| Sodium chloride | 0.6 g |
| Methyl p-hydroxybenzoate | 0.02 g |
| Chlorobutanol | 0.3 g |
| Sodium hydroxide | q.s. |
| Sterile purified water | To make 100 ml pH 5.6 |

The above ingredients are dissolved together and aseptically filtered to provide an ophthalmic solution.

| Preparation Example 3 | Oral tablet |
|---|---|
| Stearyl 3-(L-ascorbyl-2-phosphoryl)-glycyrrhetinate potassium | 100 mg |
| Lactic acid | 80 mg |
| Starch | 17 mg |
| Magnesium stearate | 3 mg |

Using the above ingredients per tablet, tablets for oral administration are manufactured by the routine molding procedure. If desired, the tablets may be sugar-coated.

| Preparation Example 4 | Cream |
|---|---|
| Lauryl 3-(L-ascorbyl-2-phosphoryl)-glycyrrhetinate potassium | 1.0 g |
| Stearic acid | 2.0 g |
| Stearyl alcohol | 7.0 g |
| Squalene | 5.0 g |
| Octyldecanol | 6.0 g |
| Polyoxyethylene (15) cetyl ether | 3.0 g |
| Glycerol monostearate | 2.0 g |

-continued

| Preparation Example 4 | Cream |
|---|---|
| Propylene glycol | 5.0 g |
| Methyl p-hydroxybenzoate | 0.2 g |
| Propyl p-hydroxybenzoate | 0.1 g |
| Sterile purified water | 68.7 g |

Using the above ingredients, a cream is manufactured by the routine procedure.

| Preparation Example 5 | Suppository |
|---|---|
| Stearyl 3-(L-ascorbyl-2-phosphoryl)-glycyrrhetinate potassium | 0.1 g |
| Tannic acid | 0.5 g |
| Cacao butter | 20 g |

Using the above ingredients per 10 units, a suppository is manufactured by the routine molding method. These suppositories are used for the treatment of hemorrhoids.

The compound of the invention can be used as an antioxidant, antiinflammatory and/or antiallergic agent advantageously in various diseases for prophylactic and therapeutic purposes. Moreover, the compound of the invention can be used in various cosmetic products for purposes of UV absorption, skin conditioning and stabilization of cosmetic ingredients, among others.

Figure 1:
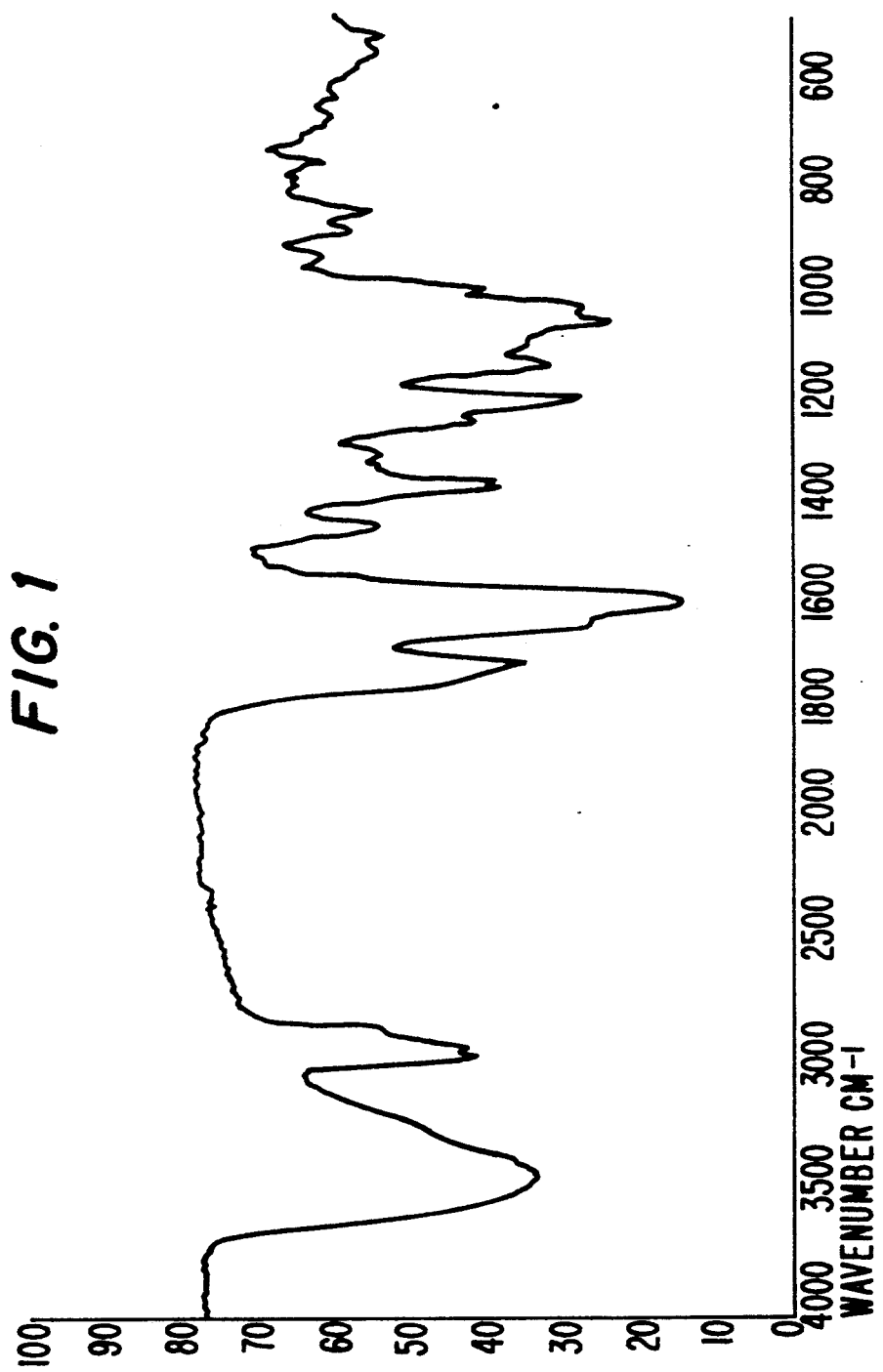
FIG. 1 is an infrared absorption spectrum (KBr) of 3-(L-ascorbyl-2-phosphoryl)-glycrrhetic acid.
Figure 2:
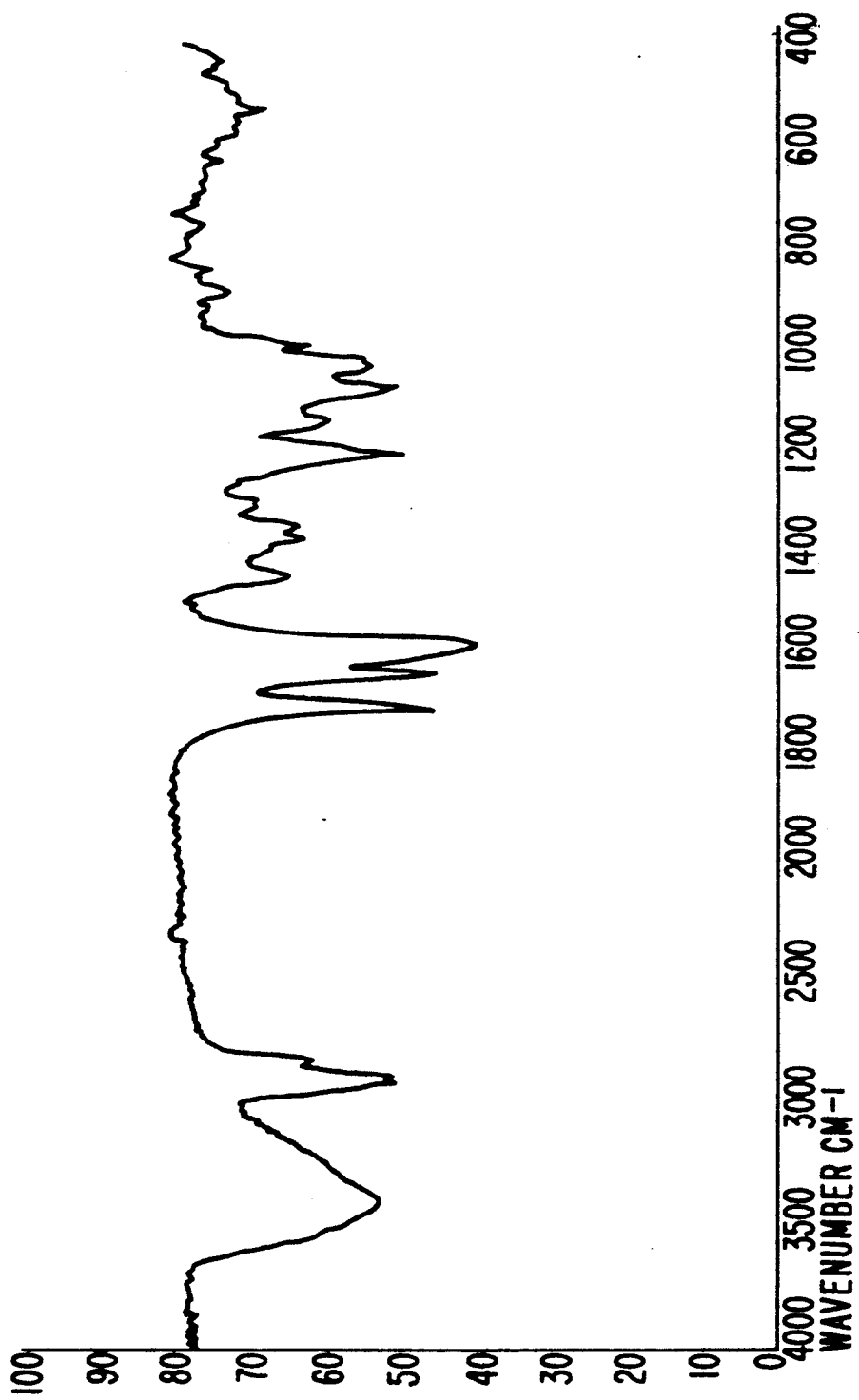
FIG. 2 is an infrared absorption spectrum (KBr) of hexyl 3-(L-ascorbyl-2-phosphoryl)-glycyrrhetinate potassium.
Figure 3:
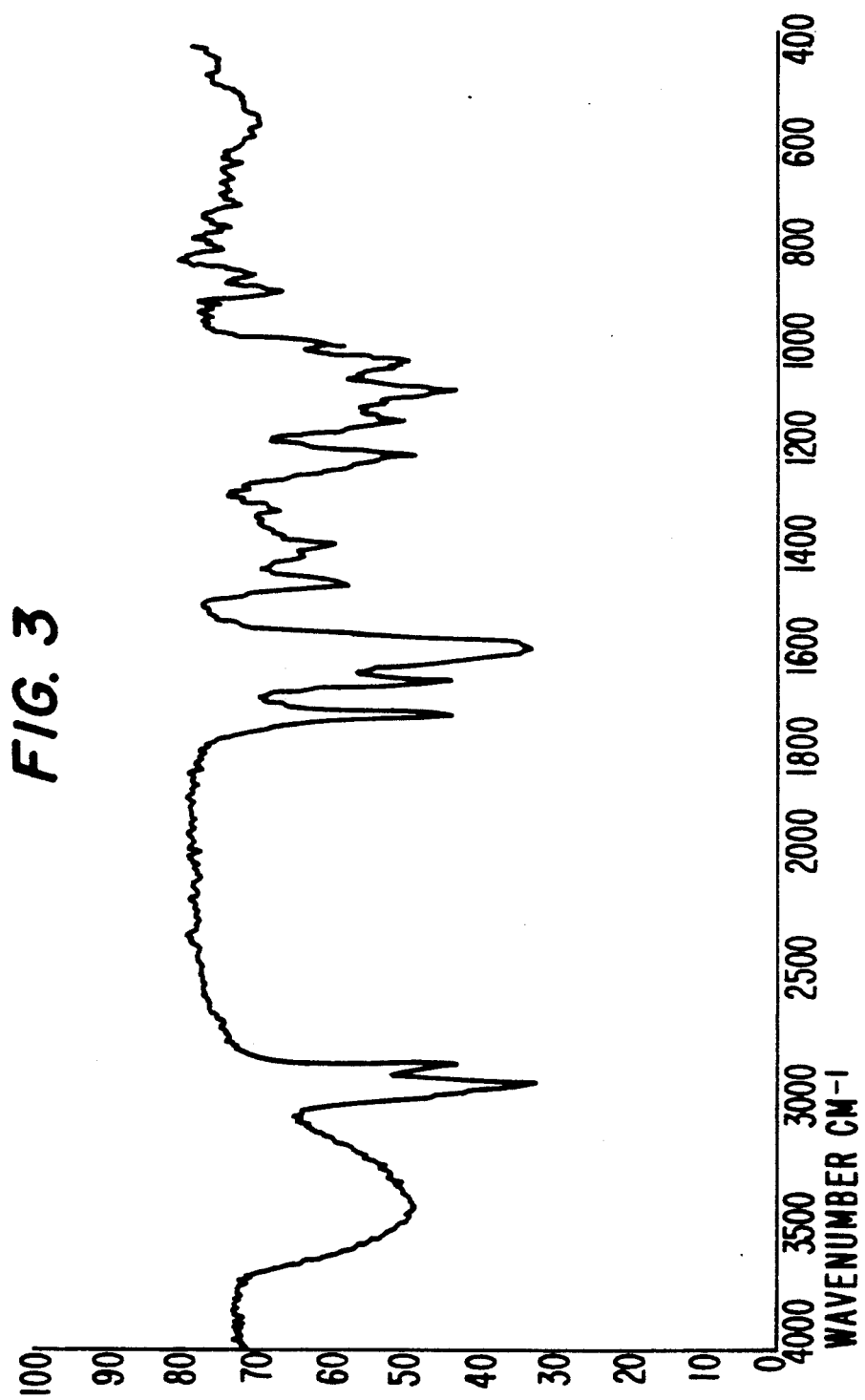
FIG. 3 is an infrared absorption spectrum (KBr) of stearyl 3-(L-ascorbyl-2-phosphoryl)-glycyrrhetinate potassium.

What is claimed is:

1. A compound of the formula

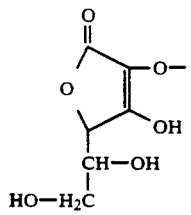
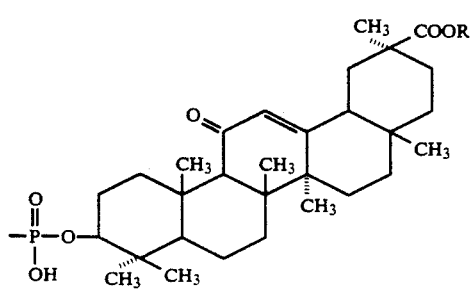

wherein R is a hydrogen atom or an alkyl group of 1 to 18 carbon atoms or a pharmacologically acceptable salt thereof.

2. A compound according to claim 1, wherein the compound is 3-(L-ascorbyl-2-phoshoryl)-glycyrrhetic acid.

3. A compound according to claim 1, wherein the compound is methyl 3-(L-ascorbyl-2-phosphoryl)-glycyrrhetinate.

4. A compound according to claim 1, wherein the compound is ethyl 3-(L-ascorbyl-2-phosphoryl)-glycyrrhetinate.

5. A compound according to claim 1, wherein the compound is hexyl 3-(L-ascorbyl-2-phosphoryl)-glycyrrhetinate potassium 6. A compound according to claim 1, wherein the compound is lauryl 3-(L-ascorbyl-2-phosphoryl)-glycyrrhetinate potassium 7. A compound according to claim 1, wherein the compound is a stearyl 3-(L-ascorbyl-2-phosphoryl)-glycyrrhetinate 8. An antioxidant, antiinflammatory and/or antiallergic composition comprising a therapeutically effective amount of a compound claimed in claim 1 and a pharmaceutically acceptable carrier therefor.

9. A composition according to claim 8, wherein the compound is 3-(L-ascorbyl-2-phosphoryl)-glycrrhetic acid 10. A composition according to claim 8, wherein the compound is methyl 3-(L-ascorbyl-2-phosphoryl)-glycrrhetinate 11. A composition according to claim 8, wherein the compound is ethyl 3-(L-ascorbyl-2-phosphoryl)-glycyrrhetinate 12. A composition according to claim 8, wherein the compound is hexyl 3-(L-ascorbyl-2-phosphoryl)-glycyrrhetinate potassium 13. A composition according to claim 8, wherein the compound is lauryl 3-(L-ascorbyl-2-phosphoryl)-glycyrrhetinate potassium 14. A composition according to claim 8, wherein the compound is stearyl 3-(L-ascorbyl-2-phosphoryl)-glycyrrhetinate 15. A composition according to claim 8, which is in the dosage form of injection, ophthalmic solution, tablet, cream or suppository.

16. A composition according to claim 9 which is in the dosage form of injection, ophthalmic solution, tablet, cream or suppository.

17. A composition according to claim 10 which is in the dosage form of injection, ophthalmic solution, tablet, cream or suppository.

18. A composition according to claim 11 which is in the dosage form of injection, ophthalmic solution, tablet, cream or suppository.

19. A composition according to claim 12 which is in the dosage form of injection, ophthalmic solution, tablet, cream or suppository.

20. A composition according to claim 13 which is in the dosage form of injection, ophthalmic solution, tablet, cream or suppository.

21. A composition according to claim 14 which is in the dosage form of injection, ophthalmic solution, tablet, cream or suppository.

* * * * *